United States Patent
Mulleners et al.

(10) Patent No.: US 6,287,841 B1
(45) Date of Patent: *Sep. 11, 2001

(54) HIGH ALKALINE SERINE PROTEASE

(75) Inventors: Leonardus Johannes Sofie Marie Mulleners, Rijen; Onno Misset, Delft; Jan Metske Van Der Laan, Breda; Franciscus Josephus Cornelius Van Gastel, Sohiedam; Cornelis Petrus Broekhuizen, Rijswijk; Erik Jan Baas, Amsterdam, all of (NL)

(73) Assignee: Genencor International, Inc., Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/090,207
(22) PCT Filed: Jul. 19, 1993
(86) PCT No.: PCT/EP93/01917
§ 371 Date: Jul. 27, 1993
§ 102(e) Date: Oct. 25, 1993
(87) PCT Pub. No.: WO94/02618
PCT Pub. Date: Feb. 3, 1994

Related U.S. Application Data

(63) Continuation-in-part of application No. 07/690,606, filed on Apr. 24, 1991, which is a continuation-in-part of application No. 07/427,103, filed on Oct. 11, 1989.

(30) Foreign Application Priority Data

Feb. 11, 1988 (EP) .................................................. 88200255
Feb. 13, 1989 (WO) .................................. PCT/NL89/00005
Jul. 17, 1992 (NL) .................................................. 92202215

(51) Int. Cl.$^7$ ............................. C12N 9/54; C12N 15/57; C12N 15/75; C12N 15/90
(52) U.S. Cl. .................... 435/221; 435/69.1; 435/252.3; 435/252.31; 435/320.1; 435/490; 536/23.9; 935/14; 935/29; 935/72; 935/74
(58) Field of Search ................................. 435/221, 222, 435/69.1, 252.3, 252.31, 320.1, 490; 536/23.2; 510/350

(56) References Cited

U.S. PATENT DOCUMENTS

| Re. 30,602 | 5/1981 | Te Nijenhuis ........................... 252/99 |
| Re. 34,606 | 5/1994 | Estell et al. ........................... 435/222 |
| 3,723,250 | 3/1973 | Aunstrup et al. ....................... 195/62 |
| 3,790,482 | 2/1974 | Jones et al. ........................... 252/525 |
| 4,242,219 | 12/1980 | Bogerman et al. ............. 252/174.12 |

(List continued on next page.)

FOREIGN PATENT DOCUMENTS

| 0126505 | 11/1984 | (EP) | ............................. C11D/3/386 |
| 0170360 | 2/1986 | (EP) | ............................. C11D/3/386 |
| 0199405 | 10/1986 | (EP) | ............................. C11D/3/386 |
| 0 220 921 | 5/1987 | (EP) . | |
| 0232169 | 8/1987 | (EP) | ................................. C12N/9/54 |
| 0238216 | 9/1987 | (EP) | ............................. C11D/3/386 |
| 0 251 446 | 1/1988 | (EP) . | |
| 0 283 075 | 2/1988 | (EP) . | |
| 0260105 * | 3/1988 | (EP) . | |
| 0284126 | 9/1988 | (EP) | ............................ C12N/15/00 |
| 0 328 229 | 8/1989 | (EP) . | |
| 0 405 901 | 1/1991 | (EP) . | |
| 0 130 756 | 1/1995 | (EP) . | |
| 2 292 042 | 6/1976 | (FR) . | |
| 1603640 | 11/1981 | (GB) | ................................ C12N/9/98 |
| 2178055A | 2/1987 | (GB) | ............................ C11D/3/386 |
| 1353317 | 5/1994 | (GB) | ................................ C07G/7/02 |
| WO 87/04461 | 7/1987 | (WO) . | |
| WO 87/05050 | 8/1987 | (WO) . | |
| 88-06624 * | 9/1988 | (WO) . | |
| WO 88/08028 | 10/1988 | (WO) . | |
| WO 88/08033 | 10/1988 | (WO) . | |
| WO 89/06279 | 7/1989 | (WO) . | |
| WO 8907642 | 8/1989 | (WO) | ................................ C12N/9/50 |
| WO 89/09819 | 10/1989 | (WO) . | |
| WO 91/00345 | 1/1991 | (WO) . | |
| 91-02792 * | 3/1991 | (WO) . | |

OTHER PUBLICATIONS

M.L. Bender et al., "The Determination of concentration . . . ", *J. Am. Chem. Soc.* (1966) 88 (24) 5890–5913.

(List continued on next page.)

*Primary Examiner*—Ponnathapu Achutamurthy
*Assistant Examiner*—William W. Moore
(74) *Attorney, Agent, or Firm*—Genencor Intl. Inc.

(57) ABSTRACT

New PB92 or Subtilisin 309 mutant serine proteases are provided having specific mutations, resulting in an surprisingly better wash performance or in an improved storage stability with at similar or even better wash performance. These PB92 or Subtilisin 309 mutants include mutations at positions 60, 87, 97, 99, 102, 116, 117, 126, 127, 128, 130, 133, 134, 154, 156, 158, 159, 160, 164, 169, 175, 180, 182, 193, 197, 198, 203, 211, and 216.

The new proteases, therefore, are very suitable for use in various types of detergents, whether or not in conjunction with other enzymes, for example amylases, cellulases and lipases. Preferred embodiments are the PB92 and Subtilisin 309 mutants having a mutation at position 102 and in particular those having at least one further mutation.

23 Claims, No Drawings

U.S. PATENT DOCUMENTS

| | | | |
|---|---|---|---|
| 4,318,818 | 3/1982 | Letton et al. | 252/174.12 |
| 4,480,037 | 10/1984 | Ichishima et al. | 435/221 |
| 4,511,490 | 4/1985 | Stanislowski et al. | 252/174.12 |
| 4,760,025 | 7/1988 | Estell et al. | 435/222 |
| 4,828,994 | 5/1989 | Fahnestock et al. | 435/172.3 |
| 4,914,031 | 4/1990 | Zukowski et al. | 435/222 |
| 4,980,288 | 12/1990 | Bryan et al. | 435/222 |
| 4,990,452 | 2/1991 | Bryan et al. | 435/222 |
| 5,013,657 | 5/1991 | Bryan et al. | 435/172.3 |
| 5,116,741 * | 5/1992 | Bryan et al. | 435/87 |
| 5,118,623 * | 6/1992 | Boguslowski et al. | 435/222 |
| 5,155,033 * | 10/1992 | Estell et al. | 435/221 |
| 5,185,258 * | 2/1993 | Caldwell et al. | 435/220 |
| 5,310,675 | 5/1994 | Estell et al. | 435/320.1 |
| 5,324,653 * | 6/1994 | Van Eckelen et al. | 435/221 |
| 5,336,611 * | 8/1994 | Van Eckelen et al. | 435/221 |
| 5,340,735 * | 8/1994 | Christianson et al. | 435/221 |
| 5,665,587 * | 9/1997 | Asslyng et al. | 435/221 |
| 5,700,676 * | 12/1997 | Bott et al. | 435/221 |
| 5,741,694 * | 4/1998 | Hastrup et al. | 435/221 |
| 5,763,257 * | 7/1998 | Bott et al. | 435/221 |
| 5,801,038 * | 9/1998 | Bott et al. | 435/221 |

OTHER PUBLICATIONS

Birnboim and Doly, "A rapid alkaline extraction . . . ", *Nucleic Acids Res.* (1979) 7(6)1513–1523.

Bott et al., "Importance of Conformational Variability . . . " *Biotechnology in Agricultural Chem.*, Le Baron et al., Eds., 139–147.

Cohen et al., "Nonchromosomal antibiotic resistance . . . ", *Proc. Natl. Acad. Sci. USA* (1972) 69 (8) 2110–2114.

E.G. Delmar et al., "A sensitive new substrate . . . ", *Anal. Biochem.* (1979) 99 (2), 316–320.

Heidecker et al., A versatile primer for DNA . . . :, *Gene*, (1980) 10, 69–73.

Kawamura and Doi, "Construction of a *Bacillus subtilis*. . . ", *J. Bacteriol.* (1984) 160 (1), 442–444.

Kramer et al., "The gapped duplex . . . ", *Nucleic Acids Res.* (1984) 12 (24), 9441–9456.

Laemmli, "Cleavage of structural proteins . . . ", *Nature*, 227 (1970) 680–685.

Lin et al., "The action of proteolytic enzymes . . . ", *J. Biol. Chem.* (1969) 244 (4), 789–793.

Markland and Smith, "The Enzymes" (Boyer, ed.) (1971) vol. 3, 561–608, Academic Press, New York.

Matsubara et al., "Subtilisin BPN'", *J. Biol. Chem.* (1965) 240 (3) 1125–1130.

Messing et al., "A system for shotgun DNA sequencing . . .", *Nucleic Acids Res.* (1981) 9 (2) 309–321.

Pak & Song, "Cloning of protease gene produced by heat–Resistant Alkalinic Bacillus in *E. coli*", *Korean J. Appl. Microbiol. Eng.* (1986) 14:517.

Power et al., "Secretion and autoproeolytic maturation of subtilism",: *Proc. Nat'l. Acad. Sci. USA*, (1986) 33:3096–3100.

Sanger et al., "DNA sequencing . . . ", *Proc. Natl. Acad. Sci. USA* (1977) 74 (12) 5463–5467.

Spizizen et al., *J. Bacteriol.* (1961) 81 (5) 741–746.

Stauffer and Etson, "The effect of subtilisin . . . ", *J. Biol. Chem.* (1969) 244 (19):5333–5338.

Sternberg et al., "Prediction of electrostatic . . . ", *Nature* (1987) 330:86–88.

Van Eekelan et al., Biol. Abstracts (1989): 110:125, Abstract 156553h.

Wolff, et al., "Laundry performance of subtilisin in proteases", Lecture given 9/92 at Subtilisin Symposium, Hamburg, Germany.

Zoller and Smith, "Oligonucleotide–Directed Mutagenesis . . . ", *Methods in Enzymology*, Colowick and Kaplan Eds., (1983) 100:468–500.

Pantoliano et al., "The Engineering of Binding Affinity at Metal Ion Binding Sites for the Stabilization of Protein . . . ", *Biochemistry* (1988) 27:8311–8317.

Carter and Wells, "Engineering Enzyme Specificity by 'Substrate–Assisted Cataylsis'", *Science* (1987) 237:394–399.

Vanee et al., "Protein–Engineering of the High Alkaline Detergent Protease Maxacal", *Comm. Jour. Com. Esp. Detrg.* (1988) 19:257–66 (Chemical Abs., (1989) 110:125, Ab. 156553B).

Reeck et al., *Cell* (1987) 50:667.

Boswell et al., *Computational Molecular Biology*, (1988) pp. 161–178, Lesk, Ed. Oxford Press, Oxford.

Meloun et al., Complete primary structure of thermitase from *Thermactinomyces vulgaris* and its structural features related to the subtilisin–type proteinases. *FEBS LETT* (1985) 183(2):195–199.

Teplyakov et al., Protein engineering of the high–alkaline serine protease PB92 from *Bacillus alcalophilus*: functional and structural consequences of mutation at the S4 substrate binding pocket. *Protein Engineering*, (1992) 5:413–420.

Van Der Laan et al., Crystal structure of the high–alkaline serine protease PB92 from *Bacillus alcalophilus*. *Protein Engineering*, (1992) 5:405–411.

Betzel et al., *J. Mol. Biol.* (1992) 223:427–455.

Siezen et al., *Protein Engineering*, (1991) 4(7):719–737.

Poulos et al., *J. Biol. Chem.* (1976) 254(4):1097–1103.

Stouffer and Etson, *J. Biol. Chem.* (1969) 214(19):5333–5338.

Jung and Mayer, *Biol. Chem.* (1985) 366:485–492.

Estell et al., *J. Biol. Chem.* (1985) 260(11):6518–6521.

Wells et al., *Proc. Natl. Acad. Sci. USA* (1987) 84:5167–5171.

Bryan et al., *Proteins, Structure, Function and Genetics* (1986) 1:326–334.

PTI—32 sequence comparsion results for sequence of PB92 protease of Jun. 26, 1992.

Wells et al. (1987) in *Protein Engineering*, Oxander et al., Eds., Alan R. Liss, Inc. New York pp. 279–287.

A–GeneSeq 6 Sequence comparsion results of Jun. 26, 1992.

Davis Prot. results of Jun. 26, 1992.

"Production of Microbial Enzymes", *Microbial Technology* (1979) 1:218–311.

Carter et al., "Engineering Subtilisin BPN for Site–specific Proteolysis" *Proteins: Structure, Function, and Gene.* (1989) 6:240–248.

Carter and Wells. "Functional Interaction Among Catalytic Residues in Subtilisin BPN" *Proteins: Structure, Function, and Gene.* (1990) 7:335–342.

Sternberg, M.J.E., 1987, Nature, 330:86–89.*

Carter, P., 1988, Nature, 332: 564–568.*

Rollence, M.L., et al., 1988, Critical Reviews in Biotechnology, 8(3): 217–224.*

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 269 amino acids
      (B) TYPE: amino acid
      (D) TOPOLOGY: linear (ii) MOLECULE TYPE: protein (xi) SEQUENCE DESCRIPTION: SEQ ID NO:1:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110
```

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:2:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO:2:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

```
Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
        210                 215                 220 la Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

HIGH ALKALINE SERINE PROTEASE

CROSS-REFERENCE TO RELATED APPLICATIONS

This application is a continuation-in-part of application Ser. No. 07/690,606, filed Apr. 24, 1991, now allowed, which is a continuation-in-part of application Ser. No. 07/427,103, filed Oct. 11, 1989, now allowed.

TECHNICAL FIELD

The present invention relates to new high alkaline serine protease mutants having improved properties for use in detergents. These properties include improved stain removing ability in laundry detergent washing compositions, improved (stain removing ability at low laundering temperature, improved stability in laundry detergents upon storage and improved stability in suds prepared from the detergents.

BACKGROUND OF THE INVENTION

Use of enzymatic additives, in particular proteolytic enzymes, in detergent compositions to enable removal of protein based soilings has been amply documented. See for example the published European Patent Applications EP-A-0220921 and EP-A-0232269, U.S. Pat. Nos. 4,480,037 and Re 30,602, and the article "Production of Microbial Enzymes", Microbial Technology, vol. 1 (1979) 281–311, Academic Press.

Detergent compositions, which are applied for hard surface cleaning, toilet cleaning, dish washing and laundry cleaning, may be in a powder, liquid or paste form. Laundry detergents are generally divided into two major types, liquids and powders.

Proteolytic enzymes are generally difficult to combine with detergent compositions. They must be stable and active during application, for example in removing proteinaceous stains from textile during washing at temperatures ranging from about 10° C. to over 60° C. Furthermore they must be stable for prolonged periods of time during storage in the detergent product. Consequently, enzymes have to be stable and functional in the presence of sequestering agents, surfactants, high alkalinity, often bleaching agents, and elevated temperature. As there exist neither universal laundry detergents nor universal washing conditions (pH, temperature, sud-concentration, water hardness) that are used all over the world, the demands on enzymes may vary based on the type of detergent in which they are used and on the washing conditions.

A commercially important group of proteases is that of the so-called high alkaline proteases, derived from alkalophilic Bacilli. The commercially available high alkaline protease product MAXACAL® (Gist-brocades/IBIS) contains the serine protease "PB92", derived from Bacillus novo sp. PB92 (see U.S. Pat. Re. No. 30,602). Its amino acid sequence is disclosed in EP-A-0283075 and EP-A-0284126. Also SAVINASE® (Novo-Nordisk) is a member of this group. SAVINASE contains the "Subtilisin 309" enzyme, which is derived from Bacillus strain NCIB 10147 (U.S. Pat. No. 3,723,750). Its amino acid sequence is disclosed in WO 89/06279, where the strain is referred to as *Bacillus lentus*. The amino acid sequences of these two proteases appear to differ only at position 85 (taking the residue numbering of the PB92 protease, which corresponds to position 87 in the BPN' numbering), where PB92 has an asparagine ("N") in the one letter amino acid code) and "Subtilisin 309" a serine ("S").

Since the PB92 protease is active in stain removing at alkaline pH-values, it is commonly used as a detergent additive, together with detergent ingredients such as surfactants, builders and oxidizing agents. The latter agents are mostly used in powder form. The detergent additive may also contain other enzymes, for example amylases, cellulases and/or lipases, as far as they are compatible with the protease. PB92 protease has a high stain removing efficiency as compared to other proteases, such as the "classic" subtilisins which are well known in the art. This means that less PB92 protease is needed to obtain the same wash performance. Sensitivity to oxidation is an important drawback of the PB92 protease and all other known serine proteases used for application in detergents.

Originally the commercially available alkaline proteases such as MAXACAL® were developed for application in detergents at enhanced temperatures in the range 40–60° C. However nowadays, because the growing emphasis on ecomomy, there is an ongoing tendency to switch to lower temperatures. As a consequence the lower wash performance at reduced temperatures, e.g. 15–25° C., is an important handicap of the excisting commercially alkaline proteases.

There are several ways of obtaining new enzymes for an intended application, which are all known to the skilled artisan. Modification of existing enzymes by protein engineering is likely to be the most popular and effective method nowadays.

The most specific way of obtaining modified enzymes is by site-directed mutagenesis, enabling specific substitution of one or more amino acids by any other desired amino acid. EP-A-0130756 exemplifies the use of this technique for generating mutant protease genes which can be expressed to give modified proteolytic enzymes. A very effective method is the oligonucleotide mediated site-directed mutagenesis, which allows a number of different mutations to be introduced at a specific part of a DNA sequence by using a single synthetic oligonucleotide preparation.

For a comprehensive summary of the various detergent compositions and enzymes, their physical forms, the conditions which the enzymes have to meet for optimal functioning, the problems and limitations of the currently available enzymes for use in detergent enzyme compositions, preparation and screening of mutant proteases, etc., reference may be made to EP-A-0328229, which is incorporated herein by reference.

WO 89/06279 claims inter alia mutants of the "Subtilisin 309" protease, in which one or more residues at the following positions are substituted (taking the original BPN' residue numbering): 6, 9, 11–12, 19, 25, 36–38, 53–59, 67, 71, 89, 104, 111, 115, 120, 121–122, 124, 128, 131, 140, 153–166, 168, 169–170, 172, 175, 180, 182, 186, 187, 191, 194, 195, 199, 218, 219, 222, 226, 234–238, 241, 260–262, 265, 268, or 275. The, number of examples in this reference describing mutants which have been actually made and tested is restricted to only eight, while no more than four positions are involved. These mutants are: S153A, G195D, G195E, N218S, [G195E M222A], [G195E M222C], M222A, and M222C.

EPA-A-0328229 discloses and claims inter alia mutant proteases which have at least 70% homology with the amino acid sequence of PB92 serine protease and differ by at least one amino acid residue at a selected site corresponding to 32, 33, 48–54, 58–62, 94–107, 116–118, 123–134, 150, 152–156, 158–161, 164, 166, 169, 175–186, 197, 198 and 203–216, 235, 243 and 259 in said PB92 serine protease, and having improved wash performance and/or improved stability relative to said PB92 serine protease. This reference is exemplified by 69 mutants, in which 17 positions are involved.

Despite the progress which seems to have been made in the past few years, there is a continuing interest in the development of new proteolytic enzymes with improved properties which make them more attractive for use in detergents. These properties may include, but are not limited to, better wash performance, improved stain removing ability at low laundering temperature, improved stability upon storage, or improved stability while they are used.

SUMMARY OF THE INVENTION

In one aspect the present invention provides new PB92 or Subtilisin 309 mutant serine protease having specific mutations, resulting in considerably improved properties which make them very suitable for application in detergents, especially laundry detergents. These PB92 or Subtilisin 309 mutants include mutations at positions 60, 87, 97, 99, 102, 116, 117, 126, 127, 128, 130, 133, 134, 154, 156, 158, 159, 160, 164, 166, 169, 175, 180, 182, 193, 197, 198, 203, 211, 212, and 216.

In a preferred embodiment of the invention there are provided PB92 and Subtilisin 309 mutants having a mutation at position 102, preferably in combination with at least one further mutation. Of these, the PB92 mutants [S99G, V102N] and [V102N, N198G] are most preferred.

In another aspect the invention provides new enzymatic detergent compositions, comprising a proteolytic enzyme product which contains at least one of such new mutant proteolytic enzyme, whether or not in conjuction with other enzymes, for example amylases, cellulases and lipases.

These and other aspects of the invention will be further outlined in the detailed description hereinafter.

DETAILED DESCRIPTION OF THE INVENTION

By the term "improved properties" as used in this specification in connection with "mutant proteases" we mean proteolytic enzymes with improved wash performance or improved stability with retained wash performance, relative to the corresponding wild-type protease.

The term "wash performance" of mutant proteases is defined in this specification as the contribution of a mutant protease to laundry cleaning additional to the effect of the detergent composition without enzyme under relevant washing conditions.

The term "relevant washing conditions" is used to indicate the conditions, particularly washing temperature, time, washing mechanics, sud concentration, type of detergent and water hardness, actually used in households in a detergent market segment.

The term "improved wash performance" is used to indicate that the wash performance of a mutant protease, on weight basis, is at least greater than 100% relative to the corresponding wild-type protease under relevant washing conditions.

The term "retained wash performance" is used to indicate that the wash performance of a mutant protease, on weight basis, is at least 80% relative to the corresponding wild-type protease under relevant washing conditions.

The term "improved stability" is used to indicate better stability of mutant proteolytic enzymes in laundry detergents during storage and/or their stability in the sud, which includes stability against oxidizing agents, sequestering agents, autolysis, surfactants and high alkalinity, relative to the corresponding wild-type enzyme.

EP-A-0328229 describes a method in which the preparation of mutant proteases is combined with an efficient selection procedure on the performance of these proteases. The test system is based on the removal of protease sensitive stains from test swatches in a launderometer or tergotometer, imitating relevant washing conditions. Suitable test swatches are, for example, the commercially available EMPA swatches. (Eidgenössische Material Prüfungs und Versuch Anstalt, St. Gallen, Switzerland) artificially soiled with proteinaceous stains. Relevant stains on swatches for testing proteases include blood, grass, chocolate, and other proteinaceous stains. The reference also discloses that in this test system other relevant factors, such as detergent composition, sud concentration, water hardness, washing mechanics, time, pH and temperature, are controlled in such a way that conditions typical for household application in a certain market segment can be imitated.

Wash performance of proteases is conveniently measured by their ability to remove certain representative stains under appropriate test conditions. This ability can be suitably determined by reflectance measurements on the test cloths, after washing with and without enzymes in a launderometer or tergotometer. The laboratory application test system according to the invention is representative for household application when used on proteases which are modified by DNA mutagenesis.

In order to practice the present invention essentially the same method can be used for the preparation, screening and selection of further mutant enzymes derived from wild-type enzymes which are produced by alkalophilic Bacilli. Preferred mutants are those encoded by a gene derived from a wild-type gene encoding the PB92 serine protease or the Subtilisin 309 serine protease and which show improved properties under the test conditions mentioned above. Also genes encoding closely related serine proteases, preferably having a homology greater than about 70%, more particularly greater than about 90%, are very suitable.

It will be clear that either oligonucleotide aided site directed mutagenesis or region directed random mutagenesis can be used or any other suitable method for efficiently generating mutations in the protease gene of choice.

In accordance with the invention, various mutants were obtained with unexpectedly improved properties, i.e. a considerably higher wash performance, improved stain removing ability at low laundering temperature, or considerably improved storage stability with a similar or even better wash performance. These improvements were surprising, since they were neither suggested by, nor could they be derived in any way from the teaching of EP-A-328229 or any other prior art, either alone or when taken together.

The present invention therefore provides a mutant protease for use in detergents which comprises:
having at least 70% homology with either the amino acid sequence of PB92 serine protease having the amino acid sequence (SEQ ID NO:1):
H$_2$N-A-Q-S-V-P-W-G-I-S-R-V-Q-A-P-A-A-H-N-R-G-L-T-G-S-G-V-K-V-A-V-L-D-T-G-I-S-T-H-P-D-L-N-I-R-G-G-A-S-F-V-P-G-E-P-S-T-Q-D-G-N-G-H-G-T-H-V-A-G-T-I-A-A-L-N-N-S-I-G-V-L-G-V-A-P-N-A-E-L-Y-A-V-K-V-L-G-A-S-G-S-G-S-V-S-S-I-A-Q-G-L-E-W-A-G-N-N-G-M-H-V-A-N-L-S-L-G-S-P-S-P-S-A-T-L-E-Q-A-V-N-S-A-T-S-R-G-V-L-V-V-A-A-S-G-N-S-G-A-G-S-I-S-Y-P-A-R-Y-A-N-A-M-A-V-G-A-T-D-Q-N-N-N-R-A-S-

F-S-Q-Y-G-A-G-L-D-I-V-A-P-G-V-N-V-Q-S-T-Y-P-G-S-T-Y-A-S-L-N-G-T-S-M-A-T-P-H-V-A-G-A-A-A-L-V-K-Q-K-N-P-S-W-S-N-V-Q-I-R-N-H-L-K-N-T-A-T-S-L-G-S-T-N-L-Y-G-S-G-L-V-N-A-E-A-A-T-R-COOH;

or the amino acid sequence of Subtilisin 309 serine protease having the amino acid sequence (SEQ ID NO:2):

H₂N-A-Q-S-V-P-W-G-I-S-R-V-Q-A-P-A-A-H-N-R-G-L-T-G-S-G-V-K-V-A-V-L-D-T-G-I-S-T-H-P-D-L-N-I-R-G-G-A-S-F-V-P-G-E-P-S-T-Q-D-G-N-G-H-G-T-H-V-A-G-T-I-A-A-L-N-N-S-I-G-V-L-G-V-A-P-S-A-E-L-Y-A-V-K-V-L-G-A-S-G-S-G-S-V-S-S-I-A-Q-G-L-E-W-A-G-N-N-G-M-H-V-A-N-L-S-L-G-S-P-S-P-S-A-T-L-E-Q-A-V-N-S-A-T-S-R-G-V-L-V-V-A-A-S-G-N-S-G-A-G-S-I-S-Y-P-A-R-Y-A-N-A-M-A-V-G-A-T-D-Q-N-N-N-R-A-S-F-S-Q-Y-G-A-G-L-D-I-V-A-P-G-V-N-V-Q-S-T-Y-P-G-S-T-Y-A-S-L-N-G-T-S-M-A-T-P-H-V-A-G-A-A-A-L-V-K-Q-K-N-P-S-W-S-N-V-Q-I-R-N-H-L-K-N-T-A-T-S-L-G-S-T-N-L-Y-G-S-G-L-V-N-A-E-A-A-T-R-COOH;

differing by at least one amino acid residue at a selected site corresponding to positions positions 60, 87, 97, 99, 102, 116, 117, 126, 127, 128, 130, 133, 134, 154, 156, 158, 159, 160, 164, 169, 175, 180, 182, 193, 197, 198, 203, 211, and 216 in said PB92 serine protease or said Subtilisin 309 serine protease, having improved wash performance and/or improved stability relative to said PB92 serine protease or said Subtilisin 309 serine protease.

A preferred group of mutant protease according to the invention are those mutants of PB92 or Subtilisin 309 protease which differ by at least one of the following mutations: [N60E], [N60E,M216S], [E87S], [S97D], [S99G], [S99G, V102I], [S99G,V102L], [S99G,V102N], [S99G,S130G], [S99G, Y203W], [S99G,M216S], [S99T], [V102A], [V102A,M216S], [V102E], [V102G], [V102H], [V102I], [V102I,G116V,S126V,P127M], [V102I,G116V, S126V,P127M],[V102I,S130G],[V102L],[V102L, G116V, S126V,P127M], [V102L,S130G), [V102L,M216F], [V102L, M216S], [V102M], [V102N], [V102N,XYZ, where XYZ is any modified amino acid], [V102N,R164Y], [V102N,N198G], [V102N,N197T,N198G], [V102N, N198G,Y203W], [V102N,Y203W], [V102N,L211E], [V102N,M216X, where X is any amino acid except M], [V102N,M216S], [V102P], [V102P,M216S], [V102Q], [V102Q,M216S], [V102S], [V102S,M216S], [V102T, [V102Y], [G116V,S126L,P127N, S128V,A156E], [G116V, S126L,P127N,S128V,Y203W], [G116V,S126L, P127Q, S128A,S160D], [G116V,S126L,P127Q,S128A,M216S], [G116V, S126N,P127S,S128A], [G116V,S126N,P127S, S128A,M216Q], [G116V, S126N,P127S,S128A,M216S], [G116V,S126R,P127Q,S128D,M216S], [G116V,S126R, P127Q,S128D,M216S], [G116V,S126V,P127E,S128K, S160D], [G116V,S126V,P127M,S160D], [G116V,S126V, P127M,N198G], [G116V,S126V,P127M,Y203W], [G116V, S126V,P127M,Y203G], [M117L], [S126F,P127X, where X is an amino acid except P], [S126M, P127A,S128G,S160D], [S126M,P127A,S128G,M216Q], [S126V,P127M], [P127E], [P127E,S128T,M216S], [P127E,Y203W], [P127E,L211E], [S130G], [S130G,Y203W], [L133I], [L133M], [L133W], [L133Y], [E134C], [S154D,S160G], [S154G,S160G], [S154E], [S154G], [S154N], [A156D], [A156E], [A156G], [S158D], [S158E], [S158E, I159L], [S168N], [S159E,I158L], [S160D,A166D,M169I], [S160D, N212D], [S160D,M216Q], [S160E], [S160G], [R164I], [R164M], [R164V], [R164Y], [D175E], [R180I], [V197L], [V197N], [V197T], [V197T,M216S], [V197W], [N198C], [N198D], [N198E], [N198G], [N198G,Y203W], [N198G, M216S], [N198Q], [N198S], [N198V], [Y203C], [Y203E], [Y203G], [Y203K], [Y203L], [Y203L,V193A], [Y203T], [Y203T,S182N], [Y203V], [Y203V,V193A], [Y203W], [Y203W,M216S], [L211E], L211X,N212Z, where X is any amino acid except L and Z is any amino acid except N], [L211E,M216S], and [N212E];

having improved wash performance and/or improved stability relative to said PB92 serine protease or said Subtilisin 309 serine protease.

Preferably, the mutant proteases according to the present invention are in substantially pure form.

According to an aspect of the invention, certain new mutant proteases show a considerably improved resistance to oxidation, whereas their wash performance is also better and in many cases significantly better than the wash performance of the corresponding wild-type protease. These mutant enzymes have in common that the methionine ("M") at position 216 is substituted by another amino acid, preferably serine ("S") or glutamine ("Q"). Also substitution by phenylalanine ("F") or alanine ("A") is suitable. Further substitutions include the positions 60, 99, 102, 116, 127, 128, 130, 154, 156, 158, 197, 198, 203, 211 and 212. Preferred enzymes are those M216S and M216Q mutants which are further substituted at position 102 or at one or more of the positions 116, 126, 127 and 128. Also M216S and M216Q mutants with substitutions at positions 197, 198 and 203 are of particular interest. Preferred mutants are [N60E,M216S], [S99G,M216S], [V102A,M216S], [V102L, M216S], [V102N,M216S], [V102P,M216S], [V102Q, M216S], [V102S,M216S], [G116V,S126L,P127Q,S128A, M216S], [G116V,S126N,P127S,S128A, M216S], [G116V, S126R,P127Q,S128D,M216S], [P127E,S128T,M216S], [V197T,M216S], [N198G,M216S], [Y203W,M216S], [L211E,M216S], [G116V,S126N,P127S,S128A,M216Q], [S126M,P127A,S128G,M216Q], [V102L,M216F].

It should be noted that EP-A-0328229 describes improved oxidation stability with retained wash performance of certain M216S and M216Q mutants of PB92 and similar high alkaline serine proteases. However this reference does not teach or suggest that the "216" mutants of PB92 or Subtilisin 309 with the above-defined mutations would result even in a significantly improved wash performance.

In another aspect of the invention certain new mutant proteases which are generally not oxidation resistant, show a considerably improved wash performance. These mutant enzymes have one or more substitutions at positions 87, 97, 99, 102, 116, 117, 126, 127, 128, 130, 133, 134, 154, 156, 158, 159, 160, 164, 166, 169, 175, 180, 182, 193, 197, 198, 203, 211 and 212. Preferred mutants are those which have at least two modifications out of these defined positions. These modifications include the positions: 99 combined with at least one additional mutation at a position selected from the group comprising positions 102, 130 or 203; 102 combined with at least one additional mutation at a position selected from the group comprising positions 87, 97, 116, 117, 126, 127, 128, 130, 133, 134, 154, 156, 158, 159, 160, 164, 166, 169, 175, 180, 182, 193, 197, 198, 203, 211 or 212, preferably with at least one additional mutation at a position selected from the group comprising positions 130, 164, 197, 198, 203 or 211; 116, 126, 127, 128 combined with at least one additional mutation at a position selected from the group comprising positions 99, 102, 130, 156, 160, 197, 198, 203, 211, 212, preferably with at least one additional mutation at a position selected from the group comprising positions 102, 156, 160, 198, 203, 211; 126 and 127, preferably with one additional mutation at a position selected from the group comprising positions 102, 156, 160, 198, 203 or 211; 130 and 203; 154 and 160; 158 and 159; 160,166 and 169; 160 and 212; 198 and 203; 203 and 182; 203 and 193; 211 and 212. Preferred mutants are [S99G,V102N], [S99G,V102L], [S99G,V102I], [S99G,S130G], [S99G,Y203W], [V102I, S130G], [V102L,S130G], [V102N,R164Y], [V102N, N198G], [V102N,N197T,N198G], [V102N,N198G, Y203W], [V102N,Y203W], [V102N,L211E], [V102I, G116V,S126V,P127M], [V102L,G116V,S126V,P127M], [G116V,S126L,P127Q,S128A,S160D], [G116V,S126L, P127N,S128V,A156E], [G116V,S126L,P127N,S128V, Y203W], [G116V,S126N,P127S,S128A], [G116V,S126V, P127E,S128K, S160D], [G116V,S126V,P127M,S160D], [G116V,S126V,P127M,N198G], [G116V,S126V,P127M, Y203W], [G116V,S126V,P127M,Y203G], [S126M,P127A, S128G,S160D], [P127E,L211E], [P127E,Y203W], [S126F, P127A], [S126F,P127D], [S126F,P127H], [S126F,P127N], [S126F,P127Q], [S126V,P127M], [S130G,Y203W], [S154G,S160G], [S154D,S160G], [S158E,I159L], [S160D, A166D,M169I], [S160D, N212D], [N198G,Y203W], [Y203T,S182N], [Y203V,V193A], [Y203L, V193A], [L211G,N212D], [L211N,N212D], [L211V,N212D], [L211Y, N212S]

In still another aspect of the invention certain new mutant PB92 and Subtilisin 309 proteases exhibit unexpected activity on cacao stains, which was in no way predictable from the prior art. Such mutant proteases have one or more substitutions at positions 102, 116, 117, 126, 127, 128, 133, 154, 156, 158, 159, 160, 164, 197, 198, 203, 211 and 216. Preferred mutants are those which have at least two modifications out of these defined positions. These modifications include the positions: 102 combined with at least one additional mutation at a position selected from the group comprising positions 164 or 211; 127 combined with at least one additional mutation selected from the group comprising positions 203 or 211 ; 154 and 160 ; 158 and 159. In addition, these modifications include position M216S and M216Q combined with at least one additional mutation at positions 102 or 211. Preferred mutants are: [V102N, R164Y], [V102N,L211E], [V102N,N198G], [P127E, Y203W], [P127E,L211E], S154G,S160G], [S154D,S160G], [S158E,I159L], [M216S,V102Q], [M216S,L211E]. In addition preferred mutants are the PB92 M216S mutants with further substitutions V102Q and L211E.

In still a further aspect of the invention certain new mutant PB92 and Subtilisn 309 proteases exhibit improved stain removing ability at lower laundering temperatures, e.g. about 20° C. These mutants have usually one or more substitutions in the PB92 or Subtilisin 309 enzyme at position 99, 102, 116, 126, 127, 128, 130, 160, 197, 198 and 203. Preferred mutants are those which have at least two modifications out of these defined positions. These modifications include the positions: 99, combined with at least one additional mutation at positions 102 or 130, preferably with a mutation at position 130; 102 combined with at least one additional mutation selected from the group comprising positions 197, 198 or 203, preferablywith at least one additional mutation at positions 99 or 198, most preferably with an additional mutation at position 99 or 198; 126 combined with at least one additional mutation at positions 116, 127, 128 or 160, preferably 126 combined with 127. Preferred mutants are [S99G,S130G], [S99G,V102N], [S99G,V102I], [V102N,N198G], [V102N,Y203W], [V102N,V197I,N198G], [S126V, P127M], [S126F,P127N], [G116V,S126V,P127M,S160D], [G116V,S126L, P127Q, S128A,S160D].

Useful mutants may also be made by combining any of the mutations or sets of mutations described in this specification. Besides, it is possible to combine useful mutations as disclosed herein with mutations at other sites, which may or may not cause a substantial change in the properties of the enzyme.

To illustrate the significance of the approach used in this invention for obtaining new proteases suited for application in laundry detergents, i.e. by using representative laundry application testing as primary selection criterion, the results of the wash performance tests of mutant PB92 proteases were compared with biochemical parameters as usually determined in protein biochemical and enzymological research. These results allow the conclusion that any relation between parameters determining affinity for defined substrates and kinetics of the proteolytic reaction and wash performance is absent.

Therefore, it is of course also possible to combine two or more mutants with different properties in one enzyme product or in the same washing process. Such combination may or may not have a synergistic effect.

The invention comprises also the use of one or more mutant proteolytic enzymes, as defined hereinbefore, in a detergent composition or in a washing process. Such detergent composition may also contain one or more other enzymes, for example an amylase, cellulase or lipase which should be compatible with the protease or proteases of choice. The selection of the best combination of enzymes usually depends on the requirements and needs of the customer, but generally does not require inventive skill.

Finally, it will be clear that by deletions or insertions of the amino acids in the protease polypeptide chain, either created artificially by mutagenesis or naturally occurring in proteases homologous to PB92 protease or Subtilisin 309, the numbering of the amino acids may change. However, it is to be understood that positions homologous to amino acid positions of PB92 protease or Subtilisin 309 will fall under the scope of the claims.

The mutant proteases according to the invention can be made in essentially the same way as described in EP-A-0328229. Also, the preparation of the genes which encode the desired mutant proteases, the cloning and expression of said genes, the choice of a suitable host, the fermentation conditions, recovery, purification, screening and selection of the enzymes, etc., are essentially the same as described in EP-A-0328229 and are well within the skill of an ordinary worker.

The following Examples are offered by way of illustration and not by way of limitation.

EXPERIMENTAL SECTION

Materials and Methods which includes construction of the mutants, production of the mutants, purification, high performance liquid chromatography (HPLC) using cation exchange resin and gel filtration column, polyacrylamide gel-electrophoresis, active-site titration and determination of the kinetic parameters are similar or identical to those described in EP-A-0328229, except when stated otherwise. The mutants which are marked in the examples with the extension$^{+DTT}$ were purified and stored in the presence of 2 mM dithiothreitol (DTT).

Example 1

The wash performance of various PB92 protease mutants as determined in a specially developed washing test which is described in detail in EP-A-0328229. In addition to the sodium-tripolyphosphate (STPP) containing powder detergent IEC-STPP in this example also a non-phosphate containing powder detergent (IEC-zeolite) was used. The typical features of both test systems which were applied to test the wash performance of the new protease mutants are summarized below:

| Washing system<br>Dosed detergent/bleach | IEC-STPP<br>4 g/l | IEC-zeolite<br>7 g/l |
|---|---|---|
| sud volume per beaker (ml) | 250 | 200 |
| temperature (° C.) | 40 | 30 |
| time (min.) | 30 | 30 |
| detergent | IEC-STPP | IEC-zeolite |
| detergent dosage (g/l) | 3.68 | 5.6 |
| Na-perborate.4aq. (g/l) | 0.32 | 1.4 |
| TAED (mg/l) | 60 | 210 |
| EMPA 116/117 (5 × 5 cm) | 2/2 | 2/2 |
| CFT AS-3 CACAO (5 × 5 cm) | 0 | 2 |
| EMPA 221 clean swatch (10 × 10 cm) | 0 | 2 |
| Stainless steel balls (φ6 mm) | 0 | 15 |
| $[Ca^{2+}]$ (mM) | 2 | 2 |
| $[Mg^{2+}]$ (mM) | 0.7 | 0.7 |
| $[NaCO_3]$ (mM) | 2.5 | 0 |

The IEC-STPP detergent powder (IEC Test Detergent Type I, Formulation May 1976) and the IEC-zeolite detergent powder (Formulation April 1988) were purchased from WFK-Testgewebe GmbH, Adlerstraβe 44, D-4150, Krefeld, Germany. The performance on cacao was measured on CFT AS-3 swatches (purchased from CFT, Center For Test Materials, PO Box 120, Vlaardingen, The Netherlands). Two mutants, E87S and E87Q, were tested in the IEC-STPP system at 10 g/l of STPP/bleach containing powder detergent as indicated in Table II. In addition performance measurements at 4 g/l were made in the IEC-STPP system which was slightly modified (indicated as ADE+ in the tables): Instead of 40° C., 30 minutes and 2 mM $Ca^{2+}$, the wash performance tests were carried out at 30° C. during 20 minutes in the presence of 5 mM $Ca^{2+}$. In addition 2 EMPA 221 swatches and 15 stainless steel balls with a 6 mm diameter were included.

The results are summarized in the accompanying Tables I, II, III.

Example 2

In order to determine the wash performance of some of the new PB92 protease mutants under conditions of low detergency to mimic typically U.S. conditions, the wash performance was determined in a washing test similar to the test described in Example 1, but with some modifications. The main characteristics of the test are summarized below:

| sud volume per beaker (ml) | 200 |
|---|---|
| time (min.) | 20 |
| detergent A dosage (g/l) | 1.3 |
| EMPA 116/117 (5 × 5 cm) | 2/2 |
| CFT AS-3 cacao (5 × 5 cm) | 2 |
| EMPA 221 clean swatch (10 × 10 cm) | 2 |
| Stainless steel balls (φ6 mm) | 15 |
| $[Ca^{2+}]$ (mM) | 2 |
| $[Mg^{2+}]$ (mM) | 0.7 |

I. Oxidation resistant PB92 M216 protease mutants - wash performance ≦1.00%
Positions involved: 60, 99, 102, 116, 126, 127, 128, 197, 198, 203, 211

| Protease mutant | STPP<br>4 g/l<br>% | zeolite<br>7 g/l<br>% | $k_{cat}$<br>1/s | $K_m$<br>mM |
|---|---|---|---|---|
| PB92, protease (unmodified) | 100 | 100 | 105 | 1.0 |
| PB92 iautant with M216B and: | | | | |
| N60E | 120 | 76[117] | 7 | 2.3 |
| S99G | | 119 | 6 | 1.3 |
| V102A | | 113 | n.d. | n.d. |
| V102L | | 125 | 20 | 2.1 |
| V102N | | 113 | 26 | 4.3 |
| V102P | | 135 | n.d. | n.d. |
| V102S | | 106 | n.d. | n.d. |
| G116V, S126L, P127Q, S128A | 100 | | 23 | 8.7 |
| G116V, S126N, P127S, S128A | 110 | | 7 | 4.4 |
| G116V, S126R, P127Q, S128D | 120 | | 7 | 1.3 |
| P127E, S128T | 160 | 45 | 5 | 1.0 |
| V197T | | 129 | 9 | 1.7 |
| N198G | | 133 | 6 | 1.2 |
| Y203W | | 132 | 13 | 1.8 |
| PB92 mutant with M216Q and: | | | | |
| G116V, S126N, P127S, S128A | 130 | 70 | 3 | 4.5 |
| S126M, P127A, S128G | 100 | 36 | 5.1 | |
| PB92 mutant with M216P and: | | | | |
| V102L | | 135 | 9 | 1.3 |

[117]Performance measured on EMPA 117.
n.d.: Not determined

II. Non-oxidation resistant PB92 protease mutants (WP > 100%)
positions involved; 87, 97, 99, 102, 116, 117, 126, 127, 128, 130, 133, 134, 154, 156, 158, 160, 164, 166, 169, 175, 180, 182, 193, 197, 198, 203, 211 and 212

| Protease mutant | STPP<br>4 g/l<br>% | zeolite<br>7 g/l<br>% | $k_{cat}$<br>1/s | $K_m$<br>mM |
|---|---|---|---|---|
| PB92 protease (unmodified) | 100 | 100 | 105 | 1.0 |
| E87S | 140[10 g/l] | 126 | 134 | 1.7 |
| E87Q | 145[10 g/l] | 115[117] | 100 | 1.3 |
| 597D | 160 | | 35 | 0.4 |
| S99G | | 170 | 63 | 0.5 |
| S99G, V102I | | 226 | 202 | 1.2 |
| S99G, V102L | | 209 | 166 | 1.0 |
| S99G, V102N | | 213 | 206 | 2.4 |
| S99G, S130G | | 190 | 64 | 1.2 |
| S99G, Y203W | | 148 | 77 | 0.6 |
| S99T | | 137 | 81 | 1.0 |
| V102A | | 110[117] | 23 | 0.3 |
| V102G | | 111 | 217 | 0.5 |
| V102H | | 106 | 78 | 0.6 |
| V102I | | 180 | 252 | 1.3 |
| V102I, G116V, S126V, P127M | | 182 | 206 | 2.5 |
| V102I, S130G | | 180 | 141 | 2.0 |
| V102L | | 180 | 194 | 0.8 |
| V102L, G116V, S126V, P127M | | 147 | 160 | 2.3 |
| V102L, S130G | | 154 | 159 | 1.7 |
| V102M | | 136 | 253 | 1.3 |
| V102N | | 170 | 199 | 2.3 |
| V102N, N198G | | 253 | 223 | 3.0 |
| V102N, N197T, N198G | | 227 | 247 | 3.1 |
| V102N, N198G, Y203W. | | 162 | 210 | 2.3 |
| V102N, Y203W | | 178 | 252 | 1.9 |
| V102P | | 145 | 13 | 0.4 |
| V102Q | | 150 | 87 | 1.0 |
| V102S | | 136 | 47 | 0.4 |

-continued

II. Non-oxidation resistant PB92 protease mutants (WP > 100%)
positions involved; 87, 97, 99, 102, 116, 117, 126, 127, 128, 130, 133,
134, 154, 156, 158, 160, 164, 166, 169, 175, 180,
182, 193, 197, 198, 203, 211 and 212

| Protease mutant | STPP 4 g/l % | zeolite 7 g/l % | $k_{cat}$ l/s | $K_m$ mM |
|---|---|---|---|---|
| V102T | | 165 | 109 | 0.9 |
| V102Y | | 124 | 275 | 0.3 |
| G116V, S126L, P127Q, S128A, S160D | 200 | | 65 | 9.1 |
| G116V, S126L, P127N, S128V, Y203W | | 138 | 253 | 3.6 |
| G116V, S126N, P127S, S128A | 130 | | 64 | 2.4 |
| G116V, S126V, P127E, S128K, S160D | 175 | | 30 | 4.4 |
| G116V, S126V, P127M, S160D | 235 | | 28 | 3.4 |
| G116V, S126V, P127M, N198G | | 159 | 162 | 1.9 |
| G116V, S126V, P127M, Y203W | | 132 | 186 | 1.4 |
| G116V, S126V, P127M, Y203G | | 108 | 154 | 1.8 |
| S126F, P127A | 130 | | 223 | 10.0 |
| S126F, P127D | 120 | | 112 | 8.2 |
| S126F, P127H | 150 | | 197 | 7.8 |
| S126F, P127N | 200 | | 80 | 3.3 |
| S126F, P127Q | 150 | | 104 | 5.0 |
| S126M, P127A, S128G, S160D | 300 | | 200 | 1.9 |
| S126V, P127M | | 200 | 191 | 1.7 |
| P127E | 200 | 140 | 137 | 1.6 |
| S130G | | 170 | 85 | 1.5 |
| S130G, Y203W | | 142 | 65 | 1.2 |
| L133W | | 125 | 274 | 1.5 |
| L133Y | | 125 | n.d. | 5.9 |
| E134C$^{+DTT}$ | | 170 | n.d. | n.d. |
| S154E | 200$^{ADE+}$ | | 36 | 1.0 |
| S154G | | 110 | 70 | 0.9 |
| S154N | | 133 | 79 | 1.1 |
| A156D | 195$^{ADE+}$ | 120 | 77 | 0.9 |
| A156G | | 104 | 61 | 0.5 |
| S158G | | 105 | 82 | 0.9 |
| S158N | | 138 | 71 | 0.6 |
| S160D, A166D, M169I | 200 | 120 | 13 | 1.2 |
| S160D, N212D | 120 | | 12 | 1.5 |
| S160G | 100 | 115$^{117}$ | 29 | 1.7 |
| R164M | | 110 | 99 | 1.0 |
| R164V | | 131 | 121 | 1.2 |
| R164Y | | 135 | 115 | 0.8 |
| D175E | | 113 | 99 | 0.9 |
| R180I | | 120 | 106 | 0.9 |
| S182N, Y203T | | 125 | 94 | 0.7 |
| V193A, Y203L | | 132 | 85 | 0.6 |
| V193A, Y203V | | 132 | 86 | 0.6 |
| V197N | | 113 | 99 | 1.0 |
| V197T | | 120 | 146 | 1.1 |
| V197W | | 115 | 62 | 0.9 |
| N198C$^{DTT}$ | | 124 | n.d. | n.d. |
| N198G | | 152 | 92 | 1.1 |
| N198G, Y203W | | 132$^{117}$ | 82 | 0.7 |
| N198S | | 125 | 84 | |
| N19BV | | 121 | 104 | 0.8 |
| Y203E | | 130 | 111 | 0.6 |
| Y203G | | 135 | 91 | 1.1 |
| Y203K | | 108 | 103 | 0.6 |
| Y203L | | 106$^{117}$ | 132 | 0.6 |
| Y203T | | 135 | 92 | 0.6 |
| Y203V | | 1.35 | 90 | 0.6 |
| Y203W | | 165 | 144 | 1.0 |
| L211E | | 164 | 9 | 0.9 |
| L211G, N212D | | 105 | 39 | 1.2 |
| L211N, N212D | | 132 | 16 | 0.7 |
| L211V, N212D | | 106 | 26 | 1.4 |
| L211Y, N212S | 123 | | 81 | 0.5 |
| N212E | 140 | | 94 | 1.2 |

[117]: Performance measured on EMPA 117.
n.d.: Not determined

III. PB92 protease mutants and their performance on cacao
Positions involved: 102, 116, 117, 126, 127, 128, 133, 154, 156, 158,
159, 160, 164, 197, 198, 203, 211 and 216

| PB92 protease mutant | Wash Performance zeolite at 7 g/l (%) | | | Kinetic parameters | |
|---|---|---|---|---|---|
| | 116 | 117 | choc | $k_{cat}$ l/s | $K_m$ mM |
| V102E | 87 | | 133 | 55 | 2.2 |
| V102N, R164Y | 108 | 87 | 124 | 247 | 2.8 |
| V102N, L211E | 101 | 80 | 142 | 48 | 2.8 |
| G116V, S126L, P127N, S128V, A156E | 108 | 73 | 118 | 170 | 2.5 |
| M117L | 126 | 120 | 147 | 64 | 0.7 |
| P127E, Y203W | 105 | 103 | 134 | 135 | 1.0 |
| P127E, L211E | 63 | 47 | 119 | 9 | 1.1 |
| L133I | 126 | | 135 | 43 | 0.7 |
| L133M | 113 | | 126 | 108 | 0.6 |
| S154D, S160G | 109 | | 116 | 32 | 1.7 |
| S154G, S160G | 124 | | 132 | 34 | 2.2 |
| A156E | 140 | 137 | 173 | 105 | 1.3 |
| S158D | 139 | 126 | 190 | 91 | 1.1 |
| S158E | 123 | 121 | 176 | 101 | 1.1 |
| S158E, I159L | 118 | 132 | 132 | 90 | 1.0 |
| S160E | 104 | 110 | 145 | 17 | 0.5 |
| R164I | 119 | 117 | 126 | 127 | 1.1 |
| V197L | 79 | 106 | 119 | 60 | 0.8 |
| N198D | 110 | 110 | 153 | 92 | 0.8 |
| N198E | 102 | 123 | 159 | 87 | 0.7 |
| N198Q | 100 | 111 | 110 | 64 | 0.7 |
| Y203C$^{+DTT}$ | 95 | 107 | 129 | n.d. | n.d. |
| PB92 mutant with M216S and: | | | | | |
| V102Q | 96 | 87 | 106 | n.d. | n.d. |
| L211E | 100 | | 127 | 2 | 1.1 |

[116]: Performance measured on EMPA 116;
[117]: Performance measured on EMPA 117.
choc: Performance measured on CFT AS-3
n.d.: Not determined The composition of Detergent A was as follows:

| ingredients | % by weight |
|---|---|
| alcohol ethoxylate | 13% |
| LAS-90 | 7% |
| polyacrylate | 1% |
| zeolite | 35% |
| Na-silicate | 3% |
| $Na_2CO_3$ | 20% |
| tri-Na-citrate.$2H_2O$ | 4% |
| $Na_2SO_4$ | 8% |
| water | to 100% |

Prior to addition of PB92 protease or mutants thereof, the pH of the wash liquor was adjusted to 10.2. The results are shown in Table IV.

In addition the wash performance of some of the mutants was determined at lower temperature. The results at 20° C. are shown in table IV. All the mutants which are shown perform significantly better at 20° C. than does the wild type under these conditions. Very surprisingly some of the mutants, such as [V102N,S99G], [V102N], [G116V, S126V, P127M,S160D] do show a better wash performance at 20° C. than at 30° C. This is opposite to what was expected from the behaviour of wild type PB92: The wash performance of PB92 goes down upon lowering the laundering temperature.

So it seems that our approach to improve the wash performance of an alkaline protease by site specific engineering can also shift the temperature at which these proteases exhibit optimal performance.

TABLE IV

Wash performance new PB92 mutants at different temperatures: wash performance (%)

| PB92 protease mutants | temperature | |
|---|---|---|
| | 30° C. | 20° C. |
| S99G | 123 | n.d. |
| S99G, S130G | 188 | 173[117] |
| V102I, S99G | 117[117] | n.d. |
| V102N, S99G | 163 | 181 |
| V102N, N198G | 168 | 169[117], 155[choc] |
| V102N, Y203W | 165 | 131 |
| V102N, V197I, N198G | 139[117] | n.d. |
| V102N | 146 | 165[117] |
| V102I | 121[117] | n.d. |
| V102L | 124[117] | n.d. |
| S126V, P427M | 179[117] | n.d. |
| S126F, P127N, | 147[117] | n.d. |
| S126V, P127M, G116V, S160D | 156 | 185 |
| S126L, P127Q, S128A, G116V, S160D | 212 | 187 |
| S126M, P127A, S128G, S160D | 158 | 143[117] |
| P127E | 103, 130[choc] | n.d. |
| S130G | 132 | n.d. |

[117]: performance measured on EMPA 117
[choc]: performance measured on CFT AS-3
n.d.: not determined In all experiments the wash performance was determined relative to the PB92 wild type protease. In addition to the above-mentioned detergent A, the wash performance was also determined in several commercial U.S. detergents. The wash results were similar.

All publications (including patent applications) mentioned in this specification are indicative to the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be apparent to one of ordinary skill in the art that many changes and modifications can be made thereto without departing from the spirit or scope of the appended claims.

What is claimed is:

1. A substantially pure mutant subtilisin which comprises;
   (i) at least one substitution of an amino acid residue in a subtilisin at an amino acid residue position corresponding to residue position 60, 175 or 197 as shown in either a first amino acid sequence as depicted in SEQ ID NO:1 or a second amino acid sequence as depicted in SEQ ID NO:2 and having improved wash performance, improved stability with retained wash performance, or improved wash performance and improved stability relative to a native PB92 subtilisin as shown in SEQ ID NO:1 or native Subtilisin 309 as shown in SEQ ID NO:2.

2. The substantially pure subtilisin mutant according to claim 1 wherein said substitution is selected from the group consisting of N60E; N60E/M216S; D175E; V197Z wherein Z is L, N, T, or W; and V102N/N197T/N198G.

3. A substantially pure mutant subtilisin which comprises;
   (i) at least one substitution of an amino acid residue in a subtilisin at an amino acid residue position corresponding to residue position 60 or 197 as shown in either a first amino acid sequence as depicted in SEQ ID NO:1 or a second amino acid sequence as depicted in SEQ ID NO:2 and
   (ii) at least one second substitution of an amino acid residue in the subtilisin at a residue position corresponding to residue position 99, 116, 117, 126, 127, 128, 133, 158, 159, 169, 175, 180, 182, 203, or 216 and having improved wash performance, improved stability with retained wash performance, or improved wash performance and improved stability relative to a native PB92 subtilisin as shown in SEQ ID NO:1 or native Subtilisin 309 as shown in SEQ ID NO:2.

4. The substantially pure subtilisin mutant according to claim 3, wherein said substitution corresponds to N60E/M216S or V197T/M216S.

5. A substantially pure mutant subtilisin which comprises;
   (i) at least one first substitution of an amino acid residue in a subtilisin at an amino acid residue position corresponding to residue position 116 or 128, as shown in either a first amino acid sequence as depicted in SEQ ID NO:1 or a second amino acid sequence as depicted in SEQ ID NO:2 and
   (ii) at least one second substitution of an amino acid residue in the subtilisin at a residue position corresponding to residue position 99, 126, 127, 133, 158 or 159, and having improved wash performance, improved stability with retained wash performance, or improved wash performance and improved stability relative to a native PB92 subtilisin as shown in SEQ ID NO:1 or native Subtilisin 309 as shown in SEQ ID NO:2.

6. The substantially pure subtilisin mutant according to claim 5, wherein said substitutions are selected from the group consisting of
   (1) G116V/S126L/P127N/S128V/Y203W;
   (2) G116V/S126L/P127Q/S128A/S160D;
   (3) G116V/S126L/P127Q/S128A/M216S;
   (4) G116V/S126N/P127S/S128A;
   (5) G116V/S126N/P127S/S128A/M216Q;
   (6) G116V/S126N/P127S/S128A/M216S;
   (7) G116V/S126R/P127Q/S128D/M216S;
   (8) G116V/S126V/P127E/S128K/S160D;
   (9) G116V/S126V/P127M/S160D;
   (10) G116V/S126V/P127M/N198G;
   (11) G116V/S126V/P127MNY203W;
   (12) G116V/S126V/P127MNY203G;
   (13) S126M/P127A/S128G/S160D;
   (14) S126M/P127A/S128G/M216Q; and
   (15) P127E/S128T/M216Q.

7. A substantially pure mutant subtilisin which comprises;
   (i) at least one first substitution of an amino acid residue in a subtilisin at an amino acid residue position corresponding to residue position 60, 116, 128, 175, or 197 as shown in either a first amino acid sequence as depicted in SEQ ID NO:1 or a second amino acid sequence as depicted in SEQ ID NO:2 and
   (ii) at least one second substitution of the amino acid residue in the subtilisin at a residue position corresponding to residue position 97, 99, 126, 127, 133, 154, 158, 159, 164, 198, or 216 and
   having improved wash performance, improved stability with retained wash performance, or improved wash performance and improved stability relative to a native PB92 subtilisin as shown in SEQ ID NO:1 or native Subtilisin 309 as shown in SEQ ID NO:2, wherein the total number of substitutions are not greater than five.

8. The substantially pure mutant subtilisin as defined in claim 7, wherein the second substitution (ii) corresponds to residue position 99, 126, 127, 133, 158, or 159.

9. The substantially pure mutant subtilisin as defined in claim 7 further comprising; a (iii) third substitution of an amino acid residue in the subtilisin at an amino acid residue position corresponding to residue position 102, 160, 198, or 216.

10. The substantially pure mutant subtilisin as defined in claim 9, wherein said substitution is V102I/G116V/S126V/P127M.

11. The substantially pure mutant subtilisin as defined in claim 9, wherein said third substitution is selected from the group consisting of V102A; V102G; V102H; V102I; V102P; V102Q; V102S; V102T; S160E; and S160G.

12. The substantially pure subtilisin mutant according to claim 9, wherein said third substitution is selected from the group consisting of N198C; N198D; N198E; N198G; N198Q; N198S and N198V.

13. The substantially pure subtilisin mutant according to claim 9 further comprising a fourth substitution wherein said third and fourth substitutions are selected from the group consisting of N198G/Y203W and N198G/M216S.

14. The substantially pure mutant subtilisin as defined in claim 9 further comprising a (iv) fourth substitution wherein said third and fourth substitutions are selected from the group consisting of (1) V102N/N198G;
(2) V102I/S130G;
(3) V102L/M216F;
(4) V102L/M216S;
(5) V102Q/M216S;
(6) V102N/L211E;
(7) V102S/M216S;
(8) V102N/M216X where X is any amino acid except M;
(9) V102N/M216S;
(10) S154D/S160G;
(11) S154G/S160G;
(12) S160D/N212D;
(13) S160D/M216Q;
(14) V102N/R164Y;
(15) V102N/Y203W; and
(16) S160D/M169I.

15. The substantially pure mutant subtilisin as defined in claim 9, wherein said second substitution is S99G and said third substitution is V102L, V102I or V102N.

16. A substantially pure mutant subtilisin which comprises; substituting an amino acid residue corresponding to position 117 or 134 in a subtilisin as shown in either a first amino acid sequence as depicted in SEQ ID NO:1 or a second amino acid sequence as depicted in SEQ ID NO:2 and having improved wash performance, improved stability with retained wash performance, or improved wash performance and improved stability relative to a native PB92 subtilisin or a native Subtilisin 309.

17. The substantially pure mutant subtilisin according to claim 16 wherein said substitution is M117L, or E134C.

18. A substantially pure mutant subtilisin which comprises:

substituting five amino acid residues in a subtilisin corresponding to G116V/S126L/P127N/S128V/A156E as shown in either a first amino acid sequence as depicted in SEQ ID NO:1 or a second amino acid sequence as depicted in SEQ ID NO:2 and having improved wash performance, improved stability with retained wash performance, or improved wash performance and improved stability relative to a native PB92 subtilisin or a native Subtilisin 309.

19. A DNA sequence encoding a mutant subtilisin as defined in any one of claims 18, 1, 3, 5, 7 and 16.

20. A method of preparing a mutant subtilisin as defined in any one of claims 18, 1, 3, 5, 7 and 16 which comprises; growing a microorganism host strain transformed with an expression vector comprising a DNA sequence encoding a mutant subtilisin whereby said mutant subtilisin is produced; and recovering said mutant subtilisin.

21. A detergent additive comprising one or more mutant subtilisins as defined in any one of claims 18, 1, 3, 5, 7 and 16 and, optionally, one or more enzymes selected from the group consisting of amylases, cellulases and lipases.

22. A detergent composition comprising one or more mutant subtilisins as defined in any one of claims 18, 1, 3, 5, 7 and 16 and, optionally, one or more enzymes selected from the group consisting of amylases, cellulases and lipases.

23. A method for washing comprising; contacting a wash with a mutant subtilisin as defined in any one of claims 18, 1, 3, 5, 7 and 16 wherein said contacting occurs at a temperature in the range of about 15° C. to about 45° C.

* * * * *